US00PP36527P3

(12) United States Plant Patent
Schoone

(10) Patent No.: US PP36,527 P3
(45) Date of Patent: Mar. 4, 2025

(54) ***PHALAENOPSIS* PLANT NAMED 'Forever Young'**

(50) Latin Name: *Phalaenopsis hybrida*
Varietal Denomination: Forever Young

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/625,172

(22) Filed: Apr. 2, 2024

(65) Prior Publication Data

US 2024/0334854 P1 Oct. 3, 2024

Related U.S. Application Data

(60) Provisional application No. 63/456,505, filed on Apr. 2, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

(56) References Cited

PUBLICATIONS https://www.orchids.org/grexes/phalaenopsis-forever-young (Retrieved online Aug. 7, 2024) (Year: 2024).*

* cited by examiner

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'Forever Young', characterized by its upright plant habit; moderately vigorous growth habit; strong flowering stems; strong leaves; freely flowering habit with typically two inflorescences developing per plant, each inflorescence with numerous flowers; flowers with light reddish purple-colored petals with darker reddish purple-colored dots; and good postproduction longevity.

2 Drawing Sheets

Figure 1:
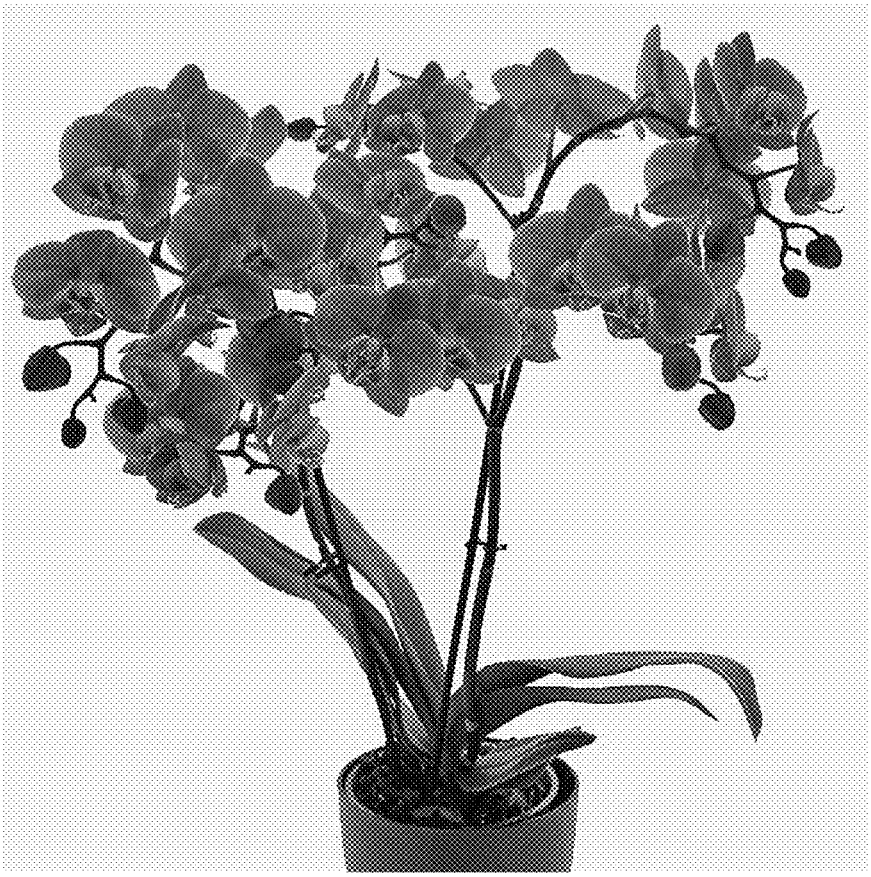

Botanical designation: *Phalaenopsis hybrida.*
Cultivar denomination: 'FOREVER YOUNG'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Feb. 27, 2023, application number 2023/0517. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Forever Young'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in April 2013 in Nantou, Taiwan of *Phalaenopsis hybrida* 'Hata Lip', not patented, as the female, or seed, parent with *Phalaenopsis hybrida* 'Schilleriana' X 'Malibu Madonna', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in December 2019.

Asexual reproduction of the new *Phalaenopsis* plant by in vitro meristem propagation in a controlled environment in Assendelft, The Netherlands since December 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Forever Young'. These characteristics in combination distinguish 'Forever Young' as a new and distinct *Phalaenopsis* plant:

1. Upright plant habit.
2. Moderately vigorous growth habit.
3. Strong flowering stems.
4. Strong leaves.
5. Freely flowering habit with typically two inflorescences developing per plant, each inflorescence with numerous flowers.
6. Flowers with light reddish purple-colored petals with darker reddish purple-colored dots.
7. Good postproduction longevity.

Plants of the new *Phalaenopsis* can be compared to plants of the female parent, 'Hata Lip'. Plants of the new *Phalaenopsis* differ primarily from plants of 'Hata Lip' in labellum color as the labellum of plants of the new *Phalaenopsis* is mostly greyish purple and dark yellow in color whereas the labellum of plants of 'Hata Lip' is mostly white in color and slightly tinged with violet. In addition, the lateral lobes of the labellum of plants of the new *Phalaenopsis* are more curved than the lateral lobes of the labellum of plants of 'Hata Lip'.

Plants of the new *Phalaenopsis* can be compared to plants of the male parent, 'Schilleriana' X 'Malibu Madonna'. Plants of the new *Phalaenopsis* differ primarily from plants of 'Schilleriana' X 'Malibu Madonna' in labellum color as the labellum of plants of the new *Phalaenopsis* is mostly greyish purple and dark yellow in color whereas the labellum of plants of 'Schilleriana' X 'Malibu Madonna' is mostly white to creamy white in color and slightly tinged with green. In addition, the petals of plants of the new *Phalaenopsis* have numerous dots whereas the petals of plants of 'Schilleriana' X 'Malibu Madonna' do not have dots.

Plants of the new *Phalaenopsis* can be compared to plants of *Phalaenopsis hybrida* 'Aquarelle', not patented. In side-by-side comparisons, plants of the new *Phalaenopsis* differ primarily from plants of 'Aquarelle' in labellum color as the labellum of plants of the new *Phalaenopsis* is mostly greyish purple and dark yellow in color whereas the labellum of plants of 'Aquarelle' is purplish red in color. In addition, the petals of plants of the new *Phalaenopsis* have numerous dots whereas the petals of plants of 'Aquarelle' do not have dots.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Forever Young' grown in a container.

Figure 2:
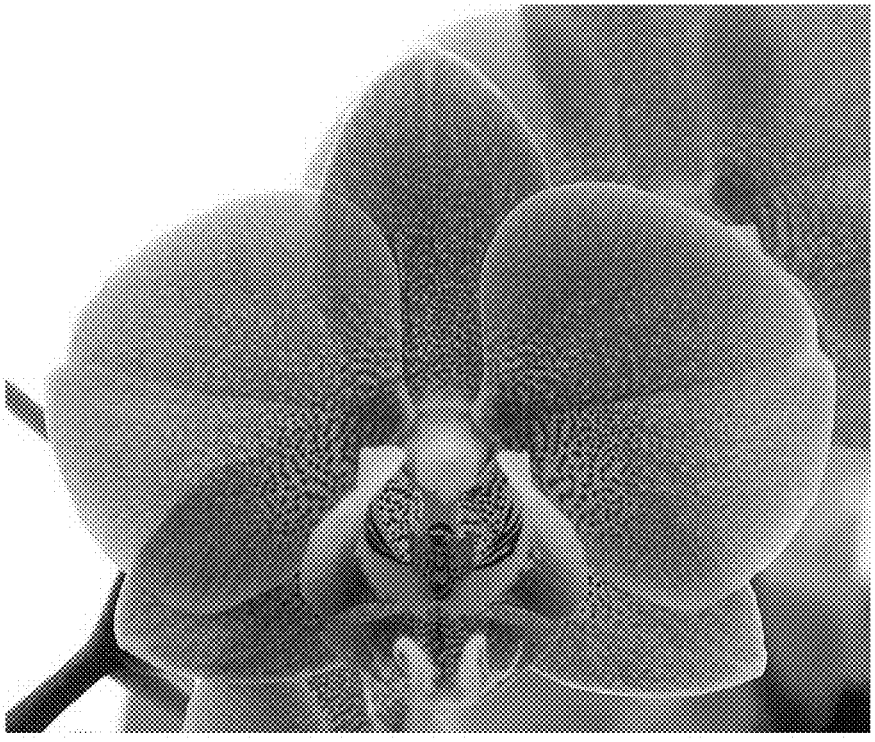

The photograph on the second sheet (FIG. 2) is a close-up view of a typical flower of 'Forever Young'.

DETAILED BOTANICAL DESCRIPTION

The aforementioned photographs and following observations and measurements describe plants grown during the winter in 12-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Forever Young'.

Parentage:

*Female, or seed, parent.*—*Phalaenopsis hybrida* 'Hata Lip', not patented.

*Male, or pollen, parent.*—*Phalaenopsis hybrida* 'Schilleriana' X 'Malibu Madonna', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane.*—About 17.9 cm.

*Plant height, substrate level to top of floral plane.*—About 37.5 cm.

*Plant diameter or spread.*—About 33.8 cm.

Leaf description:

*Arrangement and quantity.*—Distichous, simple; sessile; about four fully-developed leaves per plant.

*Length.*—About 19.4 cm.

*Width.*—About 6.8 cm.

*Aspect.*—Semi-erect and eventually outwardly arching.

*Shape.*—Narrowly elliptic-oblong to narrowly obovate; slightly carinate and apex slightly reflexed.

*Apex.*—Unequal acute.

*Base.*—Sheathing. Sheath length: About 1.7 cm. Sheath width: About 1.5 cm. Sheath color: Close to 143C.

*Margin.*—Entire; not undulate.

*Texture and luster, upper and lower surfaces.*—Smooth, glabrous; slightly glossy.

*Venation pattern.*—Camptodromous.

*Color.*—Developing leaves, upper surface: Close to 137B. Developing leaves, lower surface: Close to 146B; at the margins, close to 146A. Fully expanded leaves, upper surface: Close to NN137B; at the margins, close to 137C; venation, close to NN137B. Fully expanded leaves, lower surface: Close to 146B; at the margins, close to NN137C with edges, close to 143B; venation, close to 146A.

Inflorescence description:

*Appearance and flowering habit.*—Showy zygomorphic flowers arranged on axillary simple or branched racemes; typically two inflorescences develop per plant; each inflorescence with about 27 open flowers; flowers face outwardly on outwardly arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about eight weeks on the plant; flowers not persistent.

*Inflorescence length (lowermost flower to inflorescence apex).*—About 30.2 cm.

*Inflorescence width.*—About 24.5 cm.

*Flower buds.*—Height: About 1.6 cm. Diameter: About 1.2 cm by 1.5 cm. Shape: Broadly ovate. Color: Close to 183D; towards the base, tinged with close to 195B.

*Flower size.*—About 6.1 cm (vertical) by 7 cm (horizontal).

*Flower depth.*—About 2.5 cm.

*Petals, quantity and arrangement.*—Three, two lateral petals and one center petal transformed into a labellum.

*Lateral petals.*—Length: About 3.5 cm. Width: About 4 cm. Shape: Broadly deltoid-reniform to broadly deltoid-rhomboidal. Apex: Retuse, shallow. Margin: Entire; not undulate. Texture and luster, upper and lower surfaces: Smooth, glabrous; moderately velvety; matte. Color: When opening, upper surface: Close to 155B densely covered with fine dots, close to 72A, N78A and N78B; towards the margins, close to N78C with narrow edges, close to 76C; at the base, close to N78B. When opening, lower surface: Close to 77C and close to a blend of 77B and 77C; towards the center, tinged with close to 195C; narrow edges, close to 76D; venation, close to N77B. Fully opened, upper surface: Close to NN155D densely covered with fine dots, close to N78B and NN78C; towards the margins, close to a blend of N78C, N78D and NN78D with narrow edges, close to 76D; at the base, close to a blend of N78B and NN78B; colors do not change with subsequent development. Fully opened, lower surface: Close to N75B; towards the center, close to 76B; narrow edges, close to 76D; colors do not change with subsequent development.

*Labella.*—Appearance: Three-parted with two lateral lobes and a central lobe. Length, lateral lobes: About 2 cm. Width, lateral lobes: About 1.4 cm. Length, central lobe: About 1.8 cm. Width, central lobe: About 0.5 cm to 2 cm. Length, cirrhose tips: About 1.4 cm. Shape, lateral lobes: Obovate. Shape, central lobe: Deltoid with a slightly elongate apex. Apex, lateral lobes: Obtuse. Apex, central lobe: Cleft with two upward and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 4 mm in length, about 5 mm in width and about 6 mm in height. Color: When opening, upper surface: Lateral lobes: Close to NN155D; lower half, flushed with close to 76B; lower margin, close to 153B; at the base, axial stripes, close to 59B. Central lobe: Close to 182D with marbling and fine stripes, close to 59B to 59D; towards the base, close to 160B and at the base, close to NN155D with radial stripes, close to 60A; towards the apex and cirrhose tips, close to NN155A; main vein, close to 59A. When opening, lower surface: Lateral lobes: Close to NN155B; towards the base, close to 155C and flushed with close to 76B; lower margin, close to 153B. Central lobe: Close to 76B and slightly tinged with close to N74D; towards the base, strongly tinged with close to 151B and 151C and at the base, close to 156D; cirrhose tips, close to NN155A. Fully opened, upper surface: Lateral lobes: Close to NN155D; lower half, flushed with close to 70C and 70D; lower margin, close to 153B; at the base, axial stripes, close to 59B. Central lobe: Close to N77D with marbling and fine stripes, close to 59C and 59D; towards the base, close to 162B and at the base, close to NN155D with radial stripes, close to 60A; towards the apex and cirrhose tips, close to NN155B; main vein, close to 59A. Fully opened, lower surface: Lateral lobes: Close to NN155B; towards the base, close to 155C and flushed with close to 70C and 70D; lower margin, close to 153B. Central lobe: Close to 76B and slightly tinged with close to N74D; towards the base, strongly tinged with close to 151B and 151C and at the base, close to 156D; cirrhose tips, close to NN155A. Callosities: When developing, inner surface: Close to NN155B with fine dots and stripes, close to 59B. When developing, outer surface: Close to 151C with fine dots, close to 59B. Fully developed, inner surface: Close to NN155B with fine dots and stripes, close to 59B. Fully developed, outer surface: Close to 13A with fine dots, close to 59B.

*Sepals.*—Quantity and arrangement: Three, one upper dorsal sepal and two lower lateral sepals. Length, dorsal sepal: About 3.8 cm. Width, dorsal sepal: About 2.4 cm. Length, lateral sepals: About 3.7 cm. Width, lateral sepals: About 2.3 cm. Shape, dorsal sepal: Ovate to elliptic. Shape, lateral sepals: Ovate. Apex, dorsal and lateral sepals: Acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to 76D with dense fine dots, close to N78A and N78C. When opening, lower surface: Close to N77B; towards the center, tinged with close to 152D. Fully opened, upper surface: Close to NN155D with dense fine dots, close to N78B and NN78C; towards the apex and margins, close to N78C and N78D; narrow edges, close to 76D. Fully opened, lower surface: Close to N78C; towards the center, close to 76A. Color, lateral sepals: When opening, upper surface: Close to 76D with dense fine dots, close to N78A, N78C and 71A; towards the base, close to 145A. When opening, lower surface: Close to N77B; towards the center, tinged with close to 152D. Fully opened, upper surface: Close to NN155B with dense fine dots, close to N78B, 71A and 71B; towards the apex, close to N78D; towards the base, close to 145D. Fully opened, lower surface: Close to N78C; towards the center, close to 76A and 76B; at the base, slightly tinged with close to 151C.

*Peduncles*.—Length: About 45.5 cm. Diameter: About 6 mm. Strength: Strong. Aspect: Upright to outwardly arching. Texture and luster: Smooth, glabrous; matte. Color: Close to 146A and 146B densely covered with fine dots, close to 138B and 138C.

*Pedicels*.—Length: About 3.4 cm. Diameter: About 3 mm. Strength: Moderately strong. Aspect: About 70° From peduncle axis. Texture and luster: Smooth, glabrous; matte. Color: Close to 146C; distally, tinged with close to 177D.

*Reproductive organs*.—Androecium: Column length: About 9 mm. Column width: About 5 mm. Column color: Close to 76C; distally, close to 155B. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to N155A. Ovary length: About 1.4 cm. Ovary diameter: About 1 mm. Ovary color: Close to 149D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Forever Young' as herein illustrated and described.

* * * * *